US010905402B2

(12) United States Patent
Guenette et al.

(10) Patent No.: US 10,905,402 B2
(45) Date of Patent: Feb. 2, 2021

(54) DIAGNOSTIC GUIDANCE SYSTEMS AND METHODS

(71) Applicant: Toshiba Medical Systems Corporation, Tochigi (JP)

(72) Inventors: Gilles Daniel Joseph Guenette, Sammamish, WA (US); Yasuo Miyajima, Tokyo (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 371 days.

(21) Appl. No.: 15/221,312

(22) Filed: Jul. 27, 2016

(65) Prior Publication Data

US 2018/0028161 A1 Feb. 1, 2018

(51) Int. Cl.
*A61B 8/00* (2006.01)
*A61B 8/08* (2006.01)

(52) U.S. Cl.
CPC ............... *A61B 8/58* (2013.01); *A61B 8/463* (2013.01); *A61B 8/483* (2013.01); *A61B 8/485* (2013.01); *A61B 8/488* (2013.01); *A61B 8/5223* (2013.01); *A61B 8/5292* (2013.01)

(58) Field of Classification Search
CPC ......... A61B 8/463; A61B 8/483; A61B 8/485; A61B 8/488; A61B 8/5207; A61B 8/5223; A61B 8/5253; A61B 8/58; A61B 8/5292
See application file for complete search history.

(56) References Cited

U.S. PATENT DOCUMENTS

| 6,398,731 B1* | 6/2002 | Mumm | A61B 5/0456 600/437 |
| 2006/0135860 A1 | 6/2006 | Baker, Jr. et al. | |
| 2007/0133901 A1* | 6/2007 | Aiso | G06T 3/4053 382/294 |
| 2007/0161895 A1* | 7/2007 | Kim | A61B 8/08 600/437 |

(Continued)

FOREIGN PATENT DOCUMENTS

| EP | 1929956 A2 | 6/2008 |
| WO | 2014/191479 A1 | 12/2014 |
| WO | 2014/207642 A1 | 12/2014 |

OTHER PUBLICATIONS

Richard E. Klabunde, Velocity versus Flow of Moving Blood, Revised Apr. 28, 2014, https://www.cvphysiology.com/Hemodynamics/H013.*

*Primary Examiner* — Peter Luong
(74) *Attorney, Agent, or Firm* — Oblon, McClelland, Maier & Neustadt, L.L.P.

(57) ABSTRACT

An ultrasound apparatus includes a memory storing reference data of previous images for a selected anatomical region and a predetermined measurement count for the selected anatomical region. The ultrasound apparatus also includes processing circuitry configured to perform measurement acquisition on obtained ultrasound image data of a patient to generate at least one measurement result, display the generated at least one measurement result, calculate measurement metrics of the at least one measurement result, and display the calculated measurement metrics along with guidance for an operator of the ultrasound apparatus, the guidance being determined based on the calculated measurement metrics and the at least one measurement result.

21 Claims, 7 Drawing Sheets

(56) References Cited

U.S. PATENT DOCUMENTS

| | | | |
|---|---|---|---|
| 2007/0167777 A1* | 7/2007 | Abe | A61B 8/463 |
| | | | 600/441 |
| 2009/0005679 A1* | 1/2009 | Dala-Krishna | A61B 8/0883 |
| | | | 600/437 |
| 2012/0065510 A1 | 3/2012 | Snare et al. | |
| 2013/0225986 A1* | 8/2013 | Eggers | A61B 8/0825 |
| | | | 600/425 |
| 2014/0148808 A1* | 5/2014 | Inkpen | G01B 7/003 |
| | | | 606/80 |
| 2015/0094582 A1* | 4/2015 | Tanaka | A61B 8/06 |
| | | | 600/441 |
| 2015/0201909 A1* | 7/2015 | Yamamoto | A61B 8/4461 |
| | | | 600/442 |

\* cited by examiner

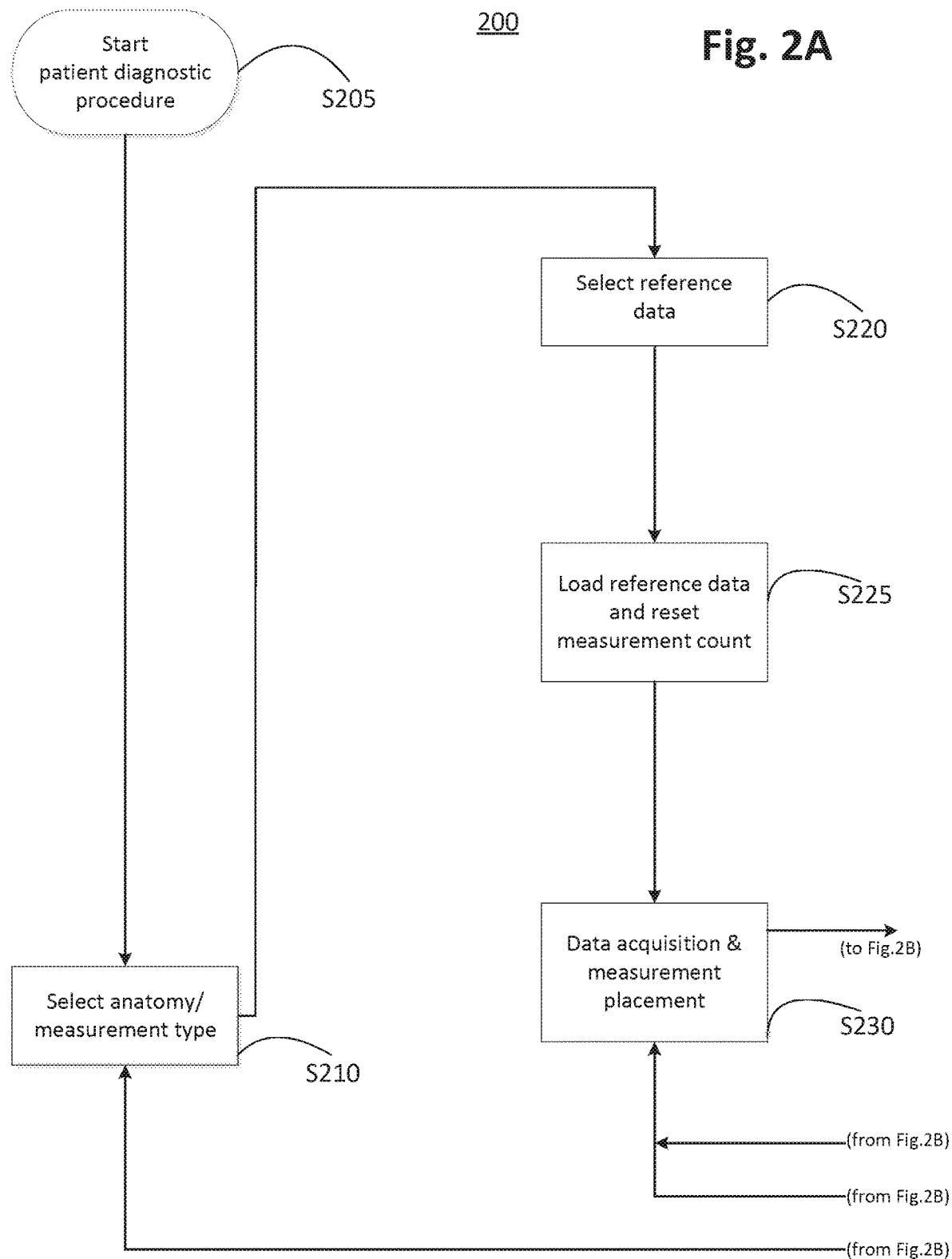

DIAGNOSTIC GUIDANCE SYSTEMS AND METHODS

BACKGROUND

Obtaining reliable medical quantification results can be difficult. Determining whether results are acceptable can require an extensive amount of experience, since each case can vary greatly. A judgment call is made many times in determining whether a result was a "bad" result because of improperly obtaining the data, subject physiology and variability, or because the data obtained displays unusual or negative results. In an effort to accommodate this uncertainty, several readings are obtained to use statistical analysis to help recognize a "bad" result and to provide more confidence in unusual or negative results. However, this is an inefficient use of equipment and personnel resources.

The "background" description provided herein is for the purpose of generally presenting the context of the disclosure. Work of the presently named inventors, to the extent it is described in this background section, as well as aspects of the description which may not otherwise qualify as conventional art at the time of filing, are neither expressly nor impliedly admitted as conventional art against the present disclosure.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2A is a first part of a flowchart of a method for providing guidance and reinforcement during a diagnostic procedure according to one embodiment;

DETAILED DESCRIPTION

Figure 1:
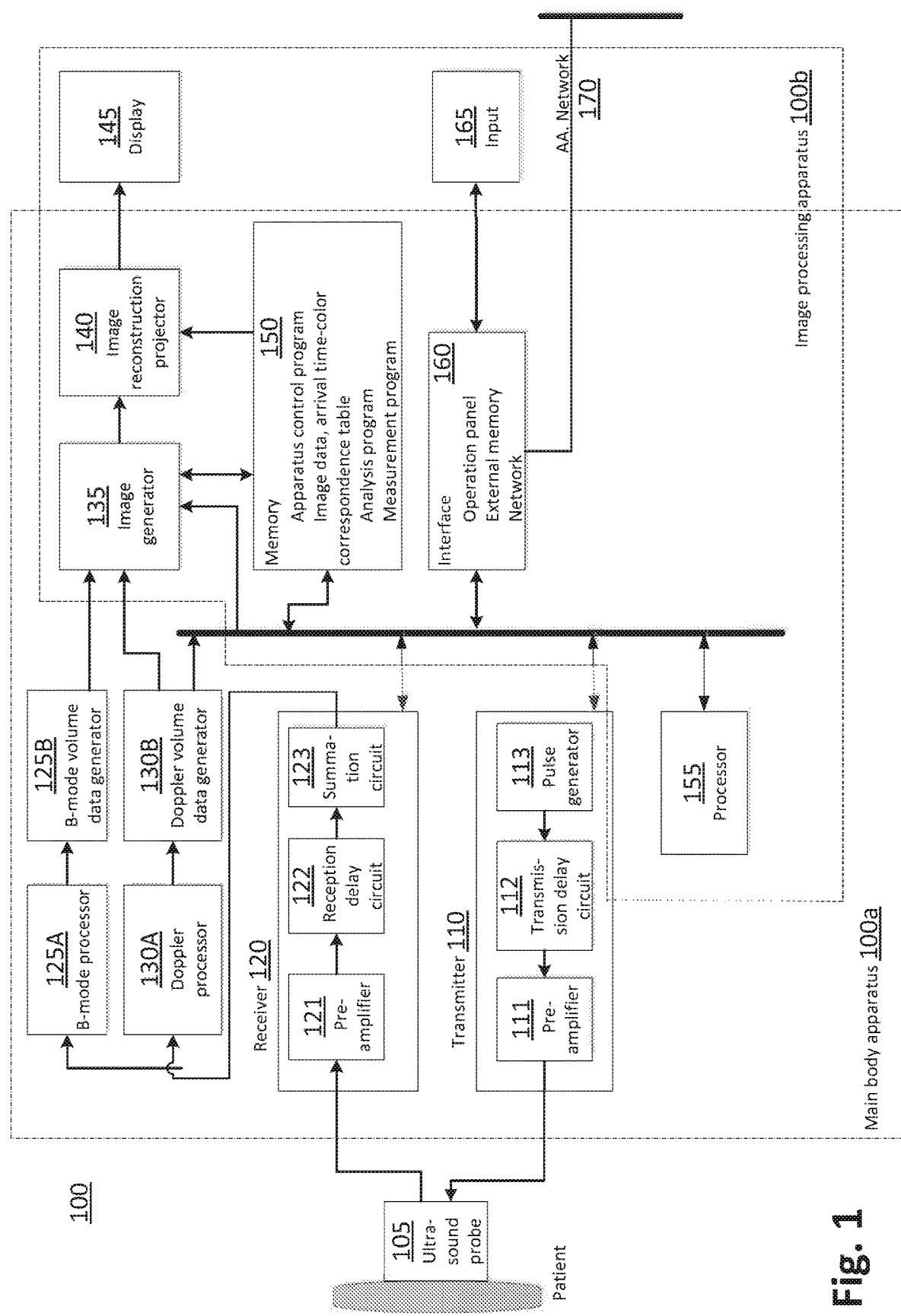
FIG. 1 is a block diagram of an ultrasound diagnosis apparatus according to one embodiment.

In one embodiment, an ultrasound apparatus includes a memory storing reference data of previous images for a selected anatomical region and a predetermined measurement count for the selected anatomical region. The ultrasound apparatus also includes processing circuitry configured to perform measurement acquisition on obtained ultrasound image data of a patient to generate at least one measurement result, display the generated at least one measurement result, calculate measurement metrics of the at least one measurement result, and display the calculated measurement metrics along with guidance for an operator of the ultrasound apparatus, the guidance being determined based on the calculated measurement metrics referring to published statistical metrics for optimized quality and the at least one measurement result.

In another embodiment, a method of determining reliable diagnostic results includes performing measurement acquisition on obtained ultrasound image data of a patient to generate at least one measurement result, displaying the at least one measurement result, and calculating measurement metrics of the at least one measurement result. The method also includes displaying the measurement metrics along with guidance for an operator of an ultrasound apparatus. The guidance is determined based on the measurement metrics in reference to published statistical metrics for optimized quality and the at least one measurement result. The method steps are executed via processing circuitry.

In another embodiment, a non-transitory computer-readable storage medium has computer-readable instructions embodied thereon, that when executed by processing circuitry causes the processing circuitry to perform a method. The method includes performing measurement acquisition on obtained ultrasound image data of a patient to generate at least one measurement result, displaying the at least one measurement result, and calculating measurement metrics of the at least one measurement result. The method also includes displaying the measurement metrics along with guidance for an operator of an ultrasound apparatus. The guidance is determined based on the measurement metrics in reference to published statistical metrics for optimized quality and the at least one measurement result.

Elastography is a medical imaging modality that maps the elastic properties of soft tissue, such as body tissue. Determining whether the body tissue is hard or soft will give diagnostic information about the presence or status of a potential disease, deformity, or other health-related issue. For example, cancerous tumors will often be harder than surrounding tissue, and diseased livers are usually stiffer than healthy livers. Ultrasound and magnetic resonance elastography (MRE) are two techniques that can be used to obtain a stiffness tissue map and an anatomical image for comparison. However, there is no quantification obtained from a map of hard versus soft body tissue.

Embodiments described herein for elastography are specific for shear wave elastography, which generates a measured value that can provide characterization of the target tissue.

Elastography, which is completely non-invasive, can be used for the investigation of many disease conditions in many organs. It can also be used to obtain diagnostic information of an anatomical image. Elastography provides tissue information that can be used to identify regions of increased or decreased stiffness or shear wave speed. Elastography can also provide values from an organ without a lesion or inclusion. It can also be used to identify a region for a biopsy by adding additional information to a diagnostic image.

Elastography can also be used to investigate diseases within the liver. Increases in liver stiffness beyond identified thresholds can be indicative of fibrosis, and the degree of fibrosis and progression to cirrhosis can be identified. Elastography can be used for detection and diagnosis of breast, thyroid, and prostate cancers, and can also be suitable for musculoskeletal imaging to determine the mechanical properties and state of muscles and tendons.

Elastography is a method of observing body tissue respond to motion, vibration, or displacement. A distortion can be caused by pushing, deforming, or vibrating the surface of the body or organ with a probe or tool. Radiation force of a focused ultrasound can be used to create a remote "push" within the tissue. A normal physiological process, such as a pulse or heartbeat, can also create a distortion.

Elastographic techniques can be categorized by which imaging modality is used to observe and induce a distortion response. Elastographic techniques include ultrasound, MRI, and pressure/stress sensors in tactile imaging (TI). The body tissue response can be an image in the form of a one-dimensional line, a two-dimensional plane, or a three-dimensional volume. The body tissue response can also be recorded as a single value, a parametric map, a slope, a video file, or a single image. The result can be compared to a normal image of the particular tissue to indicate where the imaged tissue exhibits different stiffness values when a relative value is obtained. If an absolute value is obtained, absolute value is simply reviewed for an assessment.

After the response has been observed, the relative stiffness can be displayed, along with the wave speed. The slope or Young's modulus can be calculated. Elastography techniques are based on various principles. A first principle is that, for a given applied stress force, stiffer tissue deforms, i.e., strains less than softer tissue. A second principle is that mechanical waves (specifically shear waves) travel faster through stiffer tissue than through softer tissue. Some elastography systems will display the wave speed and other techniques will compute the stiffness, such as the Young's modulus or similar shear modulus.

Medical ultrasound, also known as diagnostic sonography or ultrasonography, uses sound waves to produce ultrasonic images, also known as sonograms. The ultrasonic images are produced by sending pulses of ultrasound into tissue using an ultrasound transducer. The sound waves interact with the tissue, wherein different tissues reflect various sound waves. The echoes are processed and displayed as an image, parametric map, and/or value.

Medical ultrasound has several advantages over other diagnostic methods, e.g., provides images in real-time, is portable, is relatively lower in cost, and does not utilize ionizing radiation. Many sonographic instruments operate in the frequency range of 1 to 18 MHz, although frequencies up to 50-100 MHz have been used in special regions, such as the anterior chamber of the eye.

The choice of frequency can be a trade-off between spatial resolution of the image and imaging depth, wherein lower frequencies produce less resolution, but a deeper body image. Higher frequency sound waves have a smaller wavelength and are thus capable of reflecting or scattering from smaller structures. Higher frequency sound waves also have a large attenuation coefficient and are thus more readily absorbed into the tissue. Superficial structures, such as muscles, tendons, breast, parathyroid glands, and the neonatal brain are imaged at a higher frequency (approximately 7-18 MHz), which provides better axial and lateral resolution. Deeper structures such as the liver and kidney are imaged at a lower frequency (approximately 1-6 MHz) with lower axial and lateral resolution, but greater penetration.

An ultrasonic transducer converts ultrasound waves into electrical signals and/or vice versa by converting sound into an alternating current (AC), as well as converting an AC into sound. Attributes of a target are evaluated by interpreting the echoes from sound waves. Active ultrasonic sensors generate high-frequency sound waves and evaluate the echoes received back by the sensor. The time interval between sending the signal and receiving an echo is measured to determine the distance to an object.

Ultrasound waves can be focused either by the shape of the transducer, a lens in front of the transducer, or a complex set of control pulses from the ultrasound scanner. The focusing procures an arc-shaped sound wave from the face of the transducer. The wave travels into the body and comes into focus at a desired depth. Special materials on the face of the transducer enable the sound to be transmitted efficiently into the body by reducing acoustic mismatch. In addition, a water-based gel must placed between the patient's skin and the ultrasonic transducer. The water-based gel acts as a coupling agent between the patient's skin and the ultrasonic transducer probe to eliminate air, which causes artifacts.

The sound wave is partially reflected from the layers between different tissues or scattered from smaller structures. Sound is reflected anywhere in which there are acoustic impedance changes in the body, such as blood cells in blood plasma, small structures in organs, etc. Some of the reflections return to the transducer.

The return of the sound wave to the transducer results in the same process as sending the sound waves, except in reverse. The returned sound wave vibrates the transducer, and the transducer turns the vibrations into electrical pulses that travel to the ultrasonic scanner where they are processed and transformed into a digital image.

FIG. 1 is a block diagram illustrating the arrangement of an ultrasound diagnosis apparatus 100 according to one embodiment. The ultrasound diagnosis apparatus 100 includes an ultrasound probe 105, a transmitter 110, a receiver 120, a B-mode processor 125A, a B-mode volume data generator 125B, a Doppler processor 130A, a Doppler volume data generator 130B, a three-dimensional image generator 135, an image reconstruction projector 140, and a display 145.

The ultrasound probe 105 includes a plurality of transducers arrayed two-dimensionally. The ultrasound probe 105 receives a driving signal from the transmitter 110 and transmits ultrasonic waves to a patient. The ultrasound waves transmitted to the patient are sequentially reflected by an acoustic-impedance discontinuity surface in an internal body tissue. The ultrasound probe 105 receives the reflected ultrasound waves as an echo signal. The amplitude of this echo signal depends on an acoustic impedance difference on the discontinuity surface by which the echo signal is reflected. When the transmitted ultrasound waves are reflected by the surface of a moving patient, such as a moving blood flow or a cardiac wall, the echo signal is subjected to a frequency shift, depending on the velocity component of the moving patient in the ultrasound transmission direction, due to a Doppler effect. The ultrasound probe 105 need not always be a two-dimensional array-type probe, as long as it can perform three-dimensional scanning. For example, the ultrasound probe 105 may be a one-dimensional array-type probe, which can be mechanically swung.

The transmitter 110 repeatedly performs three-dimensional scanning of a volume to be scanned in the patient through the ultrasound probe 105. As a result of this three-dimensional scanning, the transmitter 110 outputs a plurality of echo signals with a plurality of scanning lines associated with the scanned volume.

More specifically, the transmitter 110 includes a pre-amplifier 111, a transmission delay circuit 112, and a pulse generator 113 for the transmission of ultrasound waves. The pulse generator 113 repeatedly generates rate pulses for each channel at a predetermined rate frequency. The transmission delay circuit 112 gives each rate pulse the delay time required to focus an ultrasound wave into a beam and determine transmission directivity for each channel. The pulse generator 113 applies a driving pulse to the ultrasound probe 105 at the timing based on each delayed rate pulse.

The receiver 120 includes a pre-amplifier 121, a reception delay circuit 122, and a summation circuit 123 for the reception of ultrasound waves. The pre-amplifier 121 receives echo signals from the ultrasound probe 105 and amplifies the received echo signals on a channel basis. The reception delay circuit 122 gives each echo signal converted into a digital signal the delay time required to focus the signal into a beam and determine reception directivity for each channel. The summation circuit 123 adds the respective echo signals to which the delay times are given. With this addition processing, a reflection component from a direction corresponding to the reception directivity of an echo signal is enhanced to form an ultrasound beam in accordance with the reception directivity and the transmission directivity. One ultrasound beam corresponds to one ultrasound scanning line. An echo signal for each scanning line is supplied to the B-mode processor 125A and the Doppler processor 130A.

The B-mode processor 125A logarithmically amplifies the echo signals from the receiver 120 and detects the envelope of the logarithmically-amplified echo signals to generate the data of B-mode signals representing the intensities of the echo signals. The data of the generated B-mode signals are supplied to the B-mode volume data generator 125B.

The B-mode volume data generator 125B generates volume data (to be referred to as B-mode volume data, hereinafter) associated with the patient, based on the B-mode signals from the B-mode processor 125A. More specifically, the B-mode volume data generator 125B three-dimensionally arranges the data of the B-mode signals in a memory in accordance with the position information of each scanning line, and interpolates the data of B-mode signals between the scanning lines. This arrangement processing and the interpolation processing generate B-mode volume data, constituted by a plurality of voxels. Each voxel has a voxel value corresponding to the intensity of the data of the corresponding B-mode signal.

The Doppler processor 130A frequency-analyzes each echo signal from the receiver 120 to extract a blood flow, tissue, and contrast-medium echo component by the Doppler effect, and generates the data of a Doppler signal expressing the intensity of blood flow information, such as an average velocity, variance, and power in color. The generated data of the Doppler signal is supplied to the Doppler volume data generator 130B.

The Doppler volume data generator 130B generates volume data (to be referred to as Doppler volume data, hereinafter) associated with the patient, based on each Doppler signal from the Doppler processor 130A. More specifically, the Doppler volume data generator 130B three-dimensionally arranges the data of the Doppler signals in the memory in accordance with the position information of each scanning line, and interpolates the data of Doppler signals between the scanning lines. This arrangement processing and interpolation processing generates Doppler volume data constituted by a plurality of voxels. Each voxel has a voxel value, corresponding to the intensity of the data of the corresponding Doppler signal.

The three-dimensional image generator 135 generates the data of a two-dimensional B-mode image by performing three-dimensional image processing for the B-mode volume data. The three-dimensional image generator 135 also generates the data of a two-dimensional Doppler image by performing three-dimensional image processing for the Doppler volume data. The processing of the three-dimensional image reconstruction projector 140 includes MPR (Multi-Planar Reconstruction) processing, CPR (Curved-Planar Reconstruction) processing, volume rendering, surface rendering, and MIP (Maximum Intensity Projection). The generated B-mode image data and Doppler image data are supplied to the display 145.

The display 145 displays the B-mode image from the three-dimensional image reconstruction projector 140. The display 145 also displays the Doppler image from the three-dimensional image reconstruction projector 140. The display 145 can display the B-mode image and the Doppler image, while superimposing the Doppler image on the B-mode image. The display 145 can include a display device, such as a cathode ray tube (CRT) display, liquid crystal display, organic electroluminescence display, plasma display, or the like, as needed.

The ultrasound diagnosis apparatus 100 further includes a memory 150. The memory 150 stores B-mode volume data from the B-mode volume data generator 125B and Doppler volume data from the Doppler volume data generator 130B. The data content of memory 150 includes, but is not limited to, an apparatus control program, image data, an arrival time-color correspondence table, an analysis program, and a measurement program.

The ultrasound diagnosis apparatus 100 further includes a processor 155, such as a CPU (processing circuitry). The processor 155 controls the respective structures of the ultrasound diagnosis apparatus 100. A detailed description of the processor 155 is given herein with reference to FIGS. 3-5.

FIG. 1 illustrates an interface 160, which receives an input 165. FIG. 1 also illustrates a network 170, such as an intranet or an external network, such as the Internet. Interface 160 can be configured with an operation panel, an external memory, and a network interface for communicating and operating between the main body apparatus 100*a* and the image processing apparatus 100*b*.

Table 1 illustrates results that might be obtained from a shear wave evaluation of a region of interest, such as the liver. A plurality of readings is taken, and the results are calculated for the mean, median, standard deviation, interquartile range (IQR), and the IQR/median.

TABLE 1

| | Shear Wave Results | | | | | | | | | |
|---|---|---|---|---|---|---|---|---|---|---|
| | 1 | 2 | 3 | 4 | 5 | 6 | 7 | 8 | 9 | 10 |
| Shear Wave Speed (m/s) | 2.64 | 2.72 | 3.01 | 2.74 | 2.82 | 2.69 | 4.0 | 2.78 | 2.76 | 3.03 |

Mean = 2.92
Median = 2.77
Standard deviation (SD) = 0.40
IQR = 0.30
IQR/Median = 0.11

In the results illustrated in Table 1, some manufacturers may recommend that additional measurements be obtained if the quality index (IQR/Median) is above 0.30. For example, an additional ten measurements can be obtained. However, there is no feedback pertaining to the lack of reliability of the measurements during acquisition. For less experienced users, the lack of feedback can lead to poor results.

Embodiments described herein highlight suspicious data and/or out-of-range results in each measurement obtained. Any out-of-range overall statistical measurements are highlighted. In addition, guidance statements are provided to assist with subsequent actions to take during measurement acquisition.

Figure 2B:
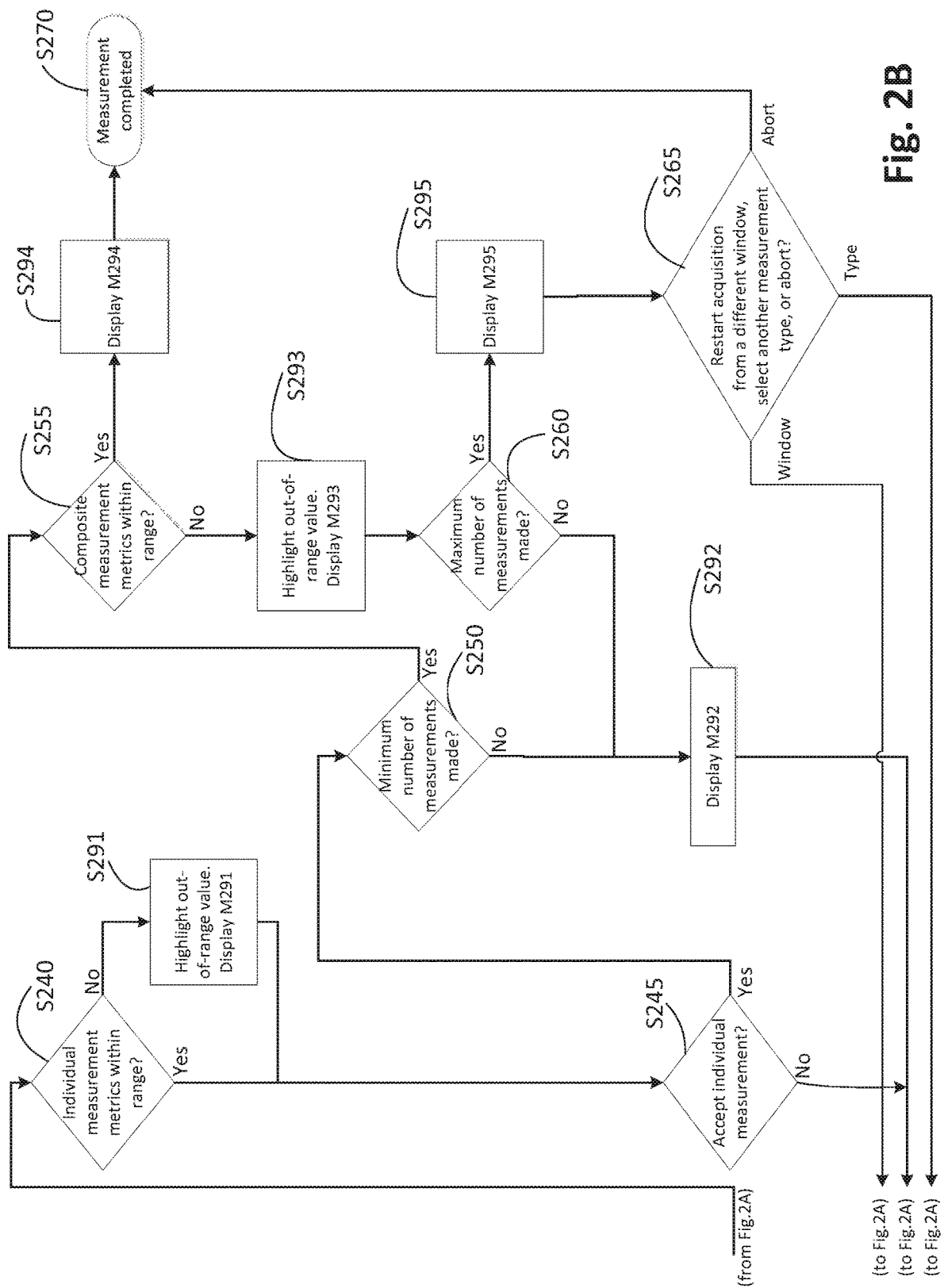
FIG. 2B is a second part of the flowchart of the method for providing guidance and reinforcement during the diagnostic procedure according to one embodiment.
Figure 2C:
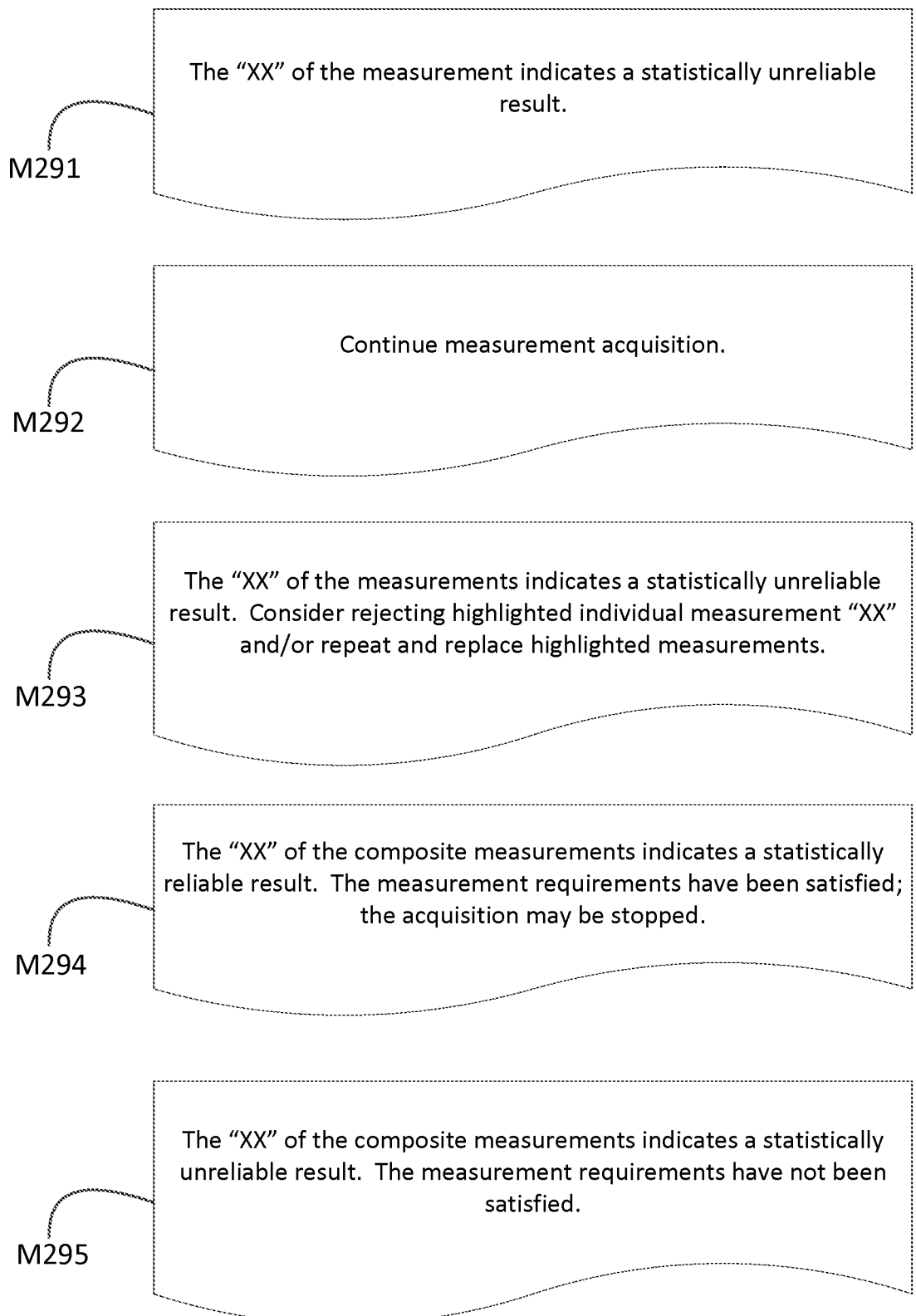
FIG. 2C is a third part of the flowchart of the method for providing guidance and reinforcement during the diagnostic procedure according to one embodiment.

FIGS. 2A, 2B, and 2C illustrate a flowchart of a method 200 for providing guidance and reinforcement during a diagnostic imaging procedure. FIGS. 2A, 2B, and 2C illustrate one flowchart and are to be viewed together as a whole. Arrows have been provided to illustrate the path of the flowchart to and from a different page of those figures.

Method 200 begins with the start of a patient diagnostic process, such as a diagnostic imaging procedure, in step S205. However, other diagnostic procedures are contemplated by embodiments described herein.

In step S210, a particular anatomy or measurement type is selected. For example, imaging of the patient's liver or other region-of-interest of the body is selected. A user or operator of the diagnostic apparatus determines which anatomical region of the patient will be interrogated and a particular measurement protocol that will be used. In another example, the processing circuitry of the diagnostic apparatus can select the region-of-interest, based upon a statistical analysis of the parametric image. The measurement protocol determines the rules or guidelines that will be followed, regarding which metrics and thresholds to be applied.

In step S220, reference data is selected from an associated database. In one example, diffuse liver reference data and associated messages are selected. In another example, liver tumor reference data and associated messages are selected. A measurement count for the selected reference data is also given. The measurement count is the number of accepted region-of-interest measurements obtained from images during an imaging encounter. In one embodiment, the measurement count is based on a statistical analysis of the selected anatomical region-of-interest from the selected reference data of previous images.

In step S225, the reference data is loaded and the measurement count is reset for the selected reference data. In one example, reference data for liver tumors is loaded and a measurement count for liver tumors is reset. One or more liver tumor related messages are also loaded to assist a user in determining if and when an acceptable number of measurements has been reached. In a second example, reference data for diffuse liver disease is loaded and a measurement count for diffuse liver disease is reset. One or more diffuse liver disease related messages are also loaded to assist a user in determining if and when an acceptable number of measurements has been reached.

In step S230, data acquisition and measurement placement for the selected reference data are implemented. Measurement acquisition is performed on obtained ultrasound image data of the selected anatomical region-of-interest for the patient to generate at least one measurement result, based upon published statistical metrics for optimized quality.

Data measurements are acquired according to the selected type of diagnostic procedure, such as a liver tumor diagnostic protocol or diffuse liver disease diagnostic protocol. The acquired data measurements are inputted into a table, via a processor of a computing device for subsequent analysis and real-time feedback. The processor and computing device are described in more detail with reference to FIG. 3. The table is further described herein with reference to Table 2.

Examples are given for two data sets, liver tumors and diffuse liver disease, for exemplary purposes only. However, several other options and their associated databases are contemplated by embodiments described herein.

After data acquisition and measurement placement have been completed in step S230, the process proceeds to step S240 in FIG. 2B, in which it is determined whether individual measurement metrics are within a pre-established range. A range for the associated data acquisition and reference data can be displayed to a user.

Embodiments herein describe a message guidance system that is applied to a selected anatomical region-of-interest. The anatomical region-of-interest can be selected by a user or operator, or by processing circuitry of the apparatus, such as an ultrasound apparatus. The guidance system is based upon a statistical analysis of a parametric image for the selected anatomical region-of-interest.

In step S291, if the individual measurement metrics are not within range (NO in step S240), a message M291 is displayed, which highlights the out-of-range value. An exemplary message M291 is illustrated in FIG. 2C, and reads, "the [actual value] of the measurement indicates a statistically unreliable result." However, other messages indicating an out-of-range or unreliable result could be displayed.

If the individual measurement metrics are within range (YES in step S240), it is determined whether to accept the individual measurement in step S245. If the individual measurement is not accepted (NO in step S245), the process proceeds back to the data acquisition and measurement placement step S230.

If the individual measurement is acceptable (YES in step S245), the process proceeds to step S250, in which it is determined whether a minimum number of measurements has been made. A count of the number of measurements can be displayed to the user.

If the minimum number of measurements has not been made (NO in step S250), a message M292 is displayed in step S292. An exemplary message M292 is illustrated in FIG. 2C, and reads, "continue measurement acquisition." A first type of failure state occurs when the minimum number of measurements has not been made. The minimum number of measurements is determined by the selected anatomy or measurement type in step S210. The minimum number of measurements is a number in which a sound statistical base has been reached for the selected anatomy or measurement type. Other messages can be displayed to indicate that measurements should continue to be taken. The process then proceeds back to data acquisition and measurement placement step S230.

If the minimum number of measurements has been made (YES in step S250), the process proceeds to step S255, in which it is determined whether composite measurement metrics are within a predetermined range. Composite measurement metrics include quality measures of a complete set of measurements, as opposed to individual measurement metrics. The range can be displayed to the user.

If composite measurement metrics are not within range (NO in step S255), a message M293 is displayed in step S293. An exemplary message M293 is illustrated in FIG. 2C, and reads, "the [actual value] of the measurements indicates a statistically unreliable result. Consider rejecting highlighted individual measurements of [actual highlighted values] and/or repeat and replace highlighted measurements." In addition, out-of-range individual measurements and out-of-range statistical measurements can be displayed to the user. However, other messages can be displayed to indicate highlighted unacceptable values, and a subsequent action to be taken. The measurement metrics are applied to individual measurements, as well as combined measurements to assess quality. When a minimum number of acquisitions has been made with an associated adequate quality level, a halt message is displayed.

If the composite measurement metrics are within range (YES in step S255), a message M294 is displayed in step S294. An exemplary message M294 is illustrated in FIG. 2C, and reads, "the [actual value] of the composite measurements indicates a statistically reliable result. The measurement requirements have been satisfied. Stop the acquisition." However, other messages can be displayed to indicate that acceptable results have been achieved and no further measurements need to be acquired.

In step S270, after displaying message M294, the measurement acquisition is completed.

In step S260, when the composite measurement metrics are not within range in step S255 and a message M293 has been displayed, it is determined whether a maximum number of statistically reliable measurements has been made. The maximum number of statistically reliable measurements can be displayed to the user. When a group of measurements is deemed to be statistically unreliable, based on a metrics analysis, the user receives a message to continue with the measurement acquisition process. When the user reaches a maximum number of measurements and the composite measurement metrics are deemed to be statistically unreliable, the user will receive an abort message.

If the maximum number of measurements has not been made (NO in step S260), the process proceeds to display message M292 to continue with measurement acquisition.

If the maximum number of measurements has been made (YES in step S260), a message M295 is displayed in step S295. An exemplary message M295 is illustrated in FIG. 2C, and reads, "the [actual value] of the composite measurements indicates a statistically unreliable result. The measurement requirements have not been satisfied." However, other messages can be displayed to indicate that acceptable results have not been obtained.

In step S265, subsequent to displaying message M295, it is determined which action to take. The process reaches step S265 when a second failure state has occurred. The second failure state is determined by a series of steps in which the minimum number of measurements has been made in step S250, but some or all of the measurements obtained were not within a statistically acceptable range in step S255, and, in addition, a maximum number of measurements has been made, which is determined in step S260. The maximum number of measurements is considered to be a number of measurements required to obtain, e.g, an adequate number of acceptable measurements or a statistically acceptable set of measurements for the selected anatomy or measurement type. When the maximum number of measurements has been reached at step S260, the user is given a message, e.g., message M295, indicating that the user should stop taking measurements and determine another course of action.

Step S265 illustrates three choices of action, including, "restart acquisition from a different window," "select another measurement type," or "abort." When the process reaches step S265, the quality of the group of measurements was not sufficient and the maximum number of attempts, according to the selected measurement protocol, was reached. If it is determined to try again from a different window, the process proceeds back to step S230 for data acquisition and measurement placement. If it is determined to try a different type of measurement acquisition, the process proceeds back to step S210 to select a particular anatomy or measurement type. If it is determined to abort, the process ends in step S270. In an alternative embodiment, step S265 could simply be to continue with the measurement acquisition.

Table 2 illustrates results according to embodiments described herein to provide more meaningful information for a shear wave region of interest (ROI) standard deviation (SD). Table 2 displays a set or group of ten individual measurements from the same window. The "Raw" values include all of the measurements. The "Final" values exclude the values the user has selected as not acceptable (bolded).

TABLE 2

| | Shear Wave Results | | | | | | | | | |
|---|---|---|---|---|---|---|---|---|---|---|
| | 1 | 2 | 3 | 4 | 5 | 6 | 7 | 8 | 9 | 10 |
| Shear Wave Speed (m/s) | 2.64 | 2.72 | 3.01 | 2.74 | 2.82 | 2.69 | 4.0 | 2.78 | 2.76 | 3.03 |
| ROI SD (m/s) | 0.88 | 0.23 | 0.92 | 0.17 | 0.29 | 0.52 | 0.74 | 0.24 | 0.31 | 0.94 |
| Accept | No | Yes | No | Yes | Yes | Yes | No | Yes | Yes | No |

| | Raw | Final |
|---|---|---|
| Mean | 2.92 | 2.75 |
| Median | 2.77 | 2.75 |
| Standard Deviation | 0.40 | 0.05 |
| IQR | 0.30 | 0.08 |
| IQR/Median | 0.11 | 0.03 |

In the results illustrated in Table 2, the standard deviation of the raw measurements indicates a statistically unreliable result. Individual measurements with a poor ROI SD or statistical outliers may be rejected, and measurements can be repeated to replace the unacceptable measurements. In the final adjusted results, the standard deviation indicates a statistically reliable result, giving confidence to the measurements.

Figure 3:
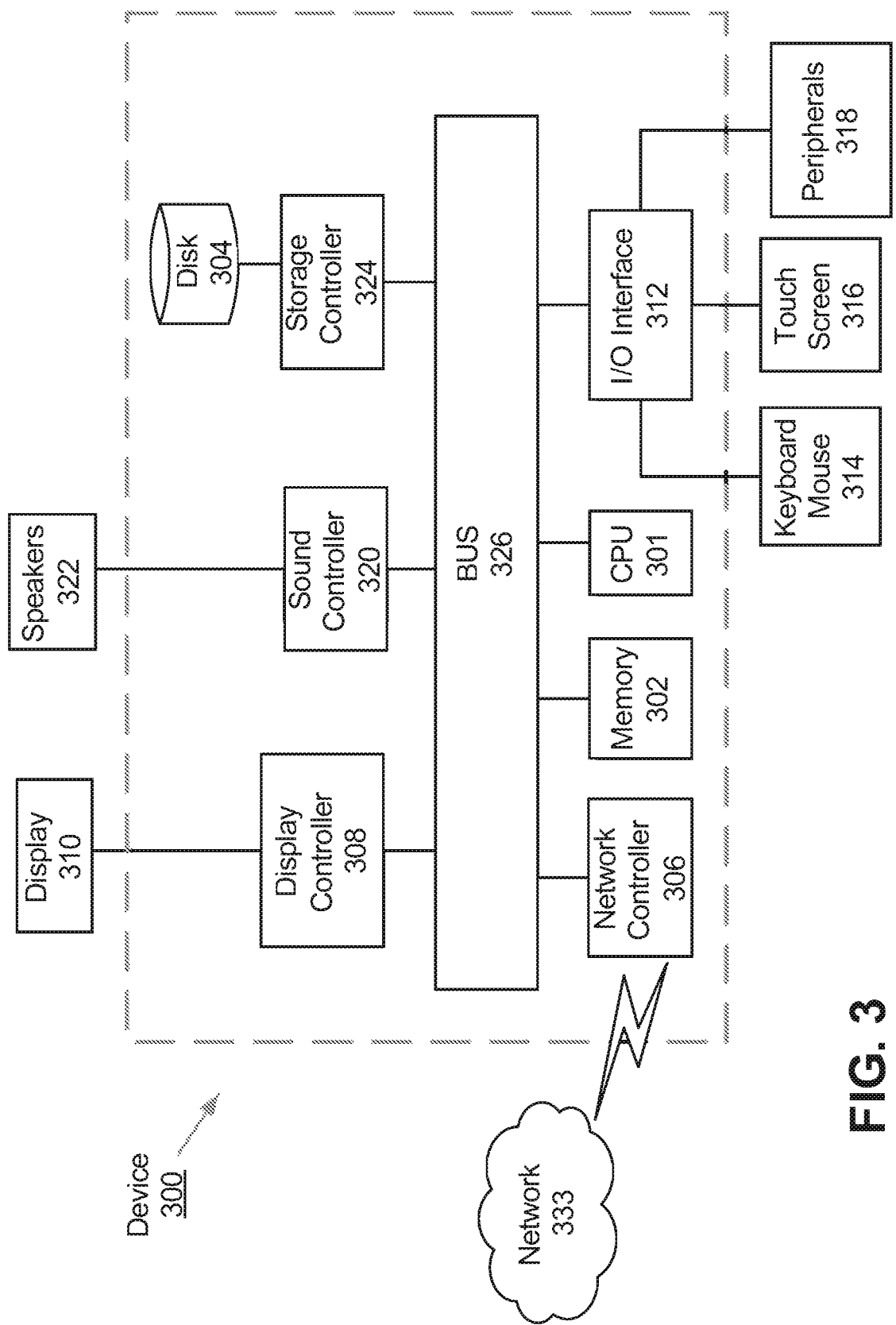
FIG. 3 illustrates an exemplary computing device according to one embodiment.

Next, a hardware description of a computing device 300, such as processor 155, is described according to exemplary embodiments, with reference to FIG. 3.

In FIG. 3, the computing device 300 includes a CPU 301 which performs the processes described above and herein after. The process data and instructions can be stored in memory 302. These processes and instructions can also be stored on a storage medium disk 304 such as a hard drive (HDD) or portable storage medium or can be stored remotely. Further, the claimed features are not limited by the form of the computer-readable media on which the instructions of the process are stored. For example, the instructions can be stored on CDs, DVDs, in FLASH memory, random access memory (RAM) read-only memory (ROM), programmable read-only memory (PROM), erasable programmable read-only memory (EPROM), electrically erasable programmable read-only memory (EEPROM), hard disk or any other information processing device with which the computing device 300 communicates, such as a server or computer.

Further, the claimed features can be provided as a utility application, background daemon, or component of an operating system, or combination thereof, executing in conjunction with CPU 301 and an operating system such as Microsoft Windows 7, UNIX, Solaris, LINUX, Apple MAC-OS and other systems known to those skilled in the art.

The hardware elements in order to achieve the computing device 300 can be realized by various circuitry elements (processing circuitry), known to those skilled in the art. For example, CPU 301 can be a Xeon or Core processor from Intel of America or an Opteron processor from AMID of America, or can be other processor types that would be recognized by one of ordinary skill in the art. Alternatively, the CPU 301 can be implemented on an FPGA, ASIC, PLD or using discrete logic circuits, as one of ordinary skill in the art would recognize. Further, CPU 301 can be implemented as multiple processors cooperatively working in parallel to perform the instructions of the inventive processes described above and below.

The computing device 300 in FIG. 3 also includes a network controller 306, such as an Intel Ethernet PRO network interface card from Intel Corporation of America, for interfacing with network 333. As can be appreciated, the network 333 can be a public network, such as the Internet, or a private network such as an LAN or WAN network, or any combination thereof and can also include PSTN or ISDN sub-networks. The network 333 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device 300 further includes a display controller 308, such as a NVIDIA GeForce GTX or Quadro graphics adaptor from NVIDIA Corporation of America for interfacing with display 310, such as a Hewlett Packard HPL2445w LCD monitor. A general purpose I/O interface 312 interfaces with a keyboard and/or mouse 314 as well as a touch screen panel 316 on or separate from display 310. General purpose I/O interface 312 also connects to a variety of peripherals 318 including printers and scanners, such as an OFFICEJET or DESKJET from Hewlett Packard.

A sound controller 320 is also provided in the computing device 300, such as SOUNDBLASTER X-FI TITANIUM from Creative, to interface with speakers/microphone 322 thereby providing and/or receiving sounds and/or music.

The general purpose storage controller 324 connects the storage medium disk 304 with communication bus 326, which can be an ISA, EISA, VESA, PCI, or similar, for interconnecting all of the components of the computing device 300. A description of the general features and functionality of the display 310, keyboard and/or mouse 314, as well as the display controller 308, storage controller 324, network controller 306, sound controller 320, and general purpose I/O interface 312 is omitted herein for brevity as these features are known.

The exemplary circuit elements described in the context of the present disclosure can be replaced with other elements and structured differently than the examples provided herein. Moreover, circuitry configured to perform features described herein can be implemented in multiple circuit units (e.g., chips), or the features can be combined in circuitry on a single chipset, as shown on FIG. 4. The chipset of FIG. 4 can be implemented in conjunction with either electronic device 100 or computing device 300 described above with reference to FIGS. 1 and 3, respectively.

Figure 4:
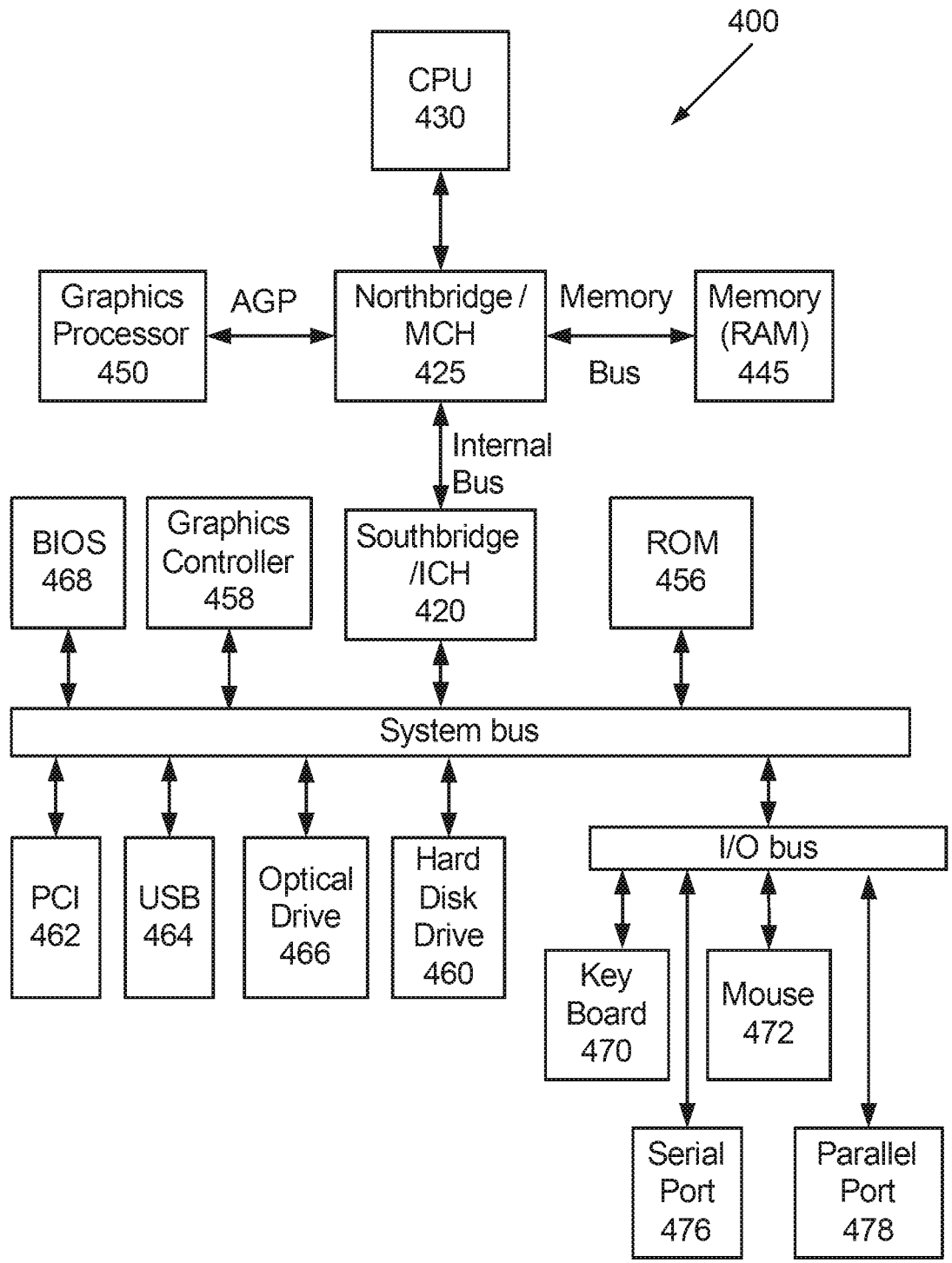
FIG. 4 is a schematic diagram of a data processing system according to one embodiment.

FIG. 4 shows a schematic diagram of a data processing system, according to certain embodiments, for performing menu navigation, as described above. The data processing system is an example of a computer in which code or instructions implementing the processes of the illustrative embodiments can be located.

In FIG. 4, data processing system 400 employs an application architecture including a northbridge and memory controller application (NB/MCH) 425 and a southbridge and input/output (I/O) controller application (SB/ICH) 420. The central processing unit (CPU) 430 is connected to NB/MCH 425. The NB/MCH 425 also connects to the memory 445 via a memory bus, and connects to the graphics processor 450 via an accelerated graphics port (AGP). The NB/MCH 425 also connects to the SB/ICH 420 via an internal bus (e.g., a unified media interface or a direct media interface). The CPU 430 can contain one or more processors and even can be implemented using one or more heterogeneous processor systems.

Figure 5:
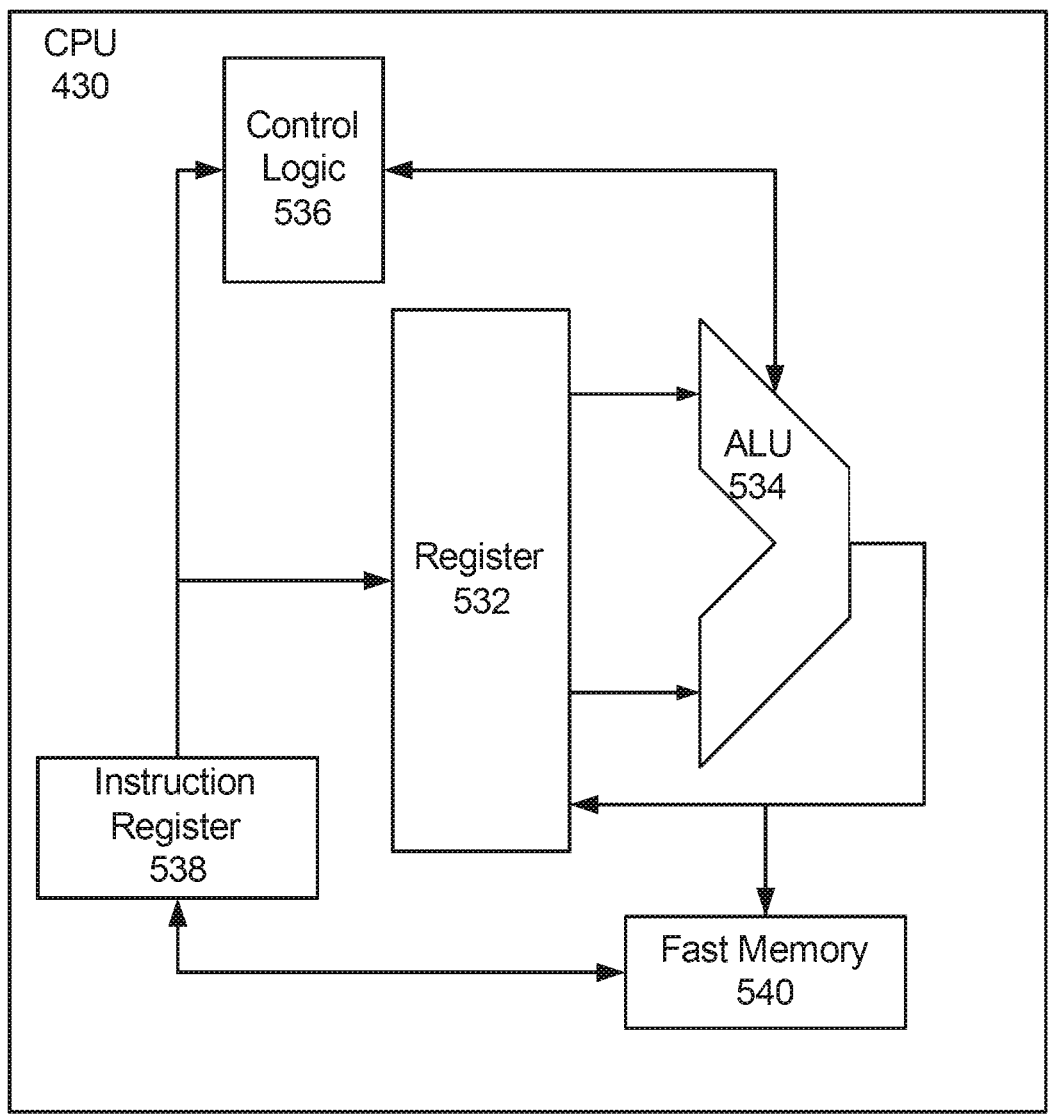
FIG. 5 illustrates an exemplary central processing unit according to one embodiment.

For example, FIG. 5 shows one implementation of CPU 430. In one implementation, an instruction register 538 retrieves instructions from a fast memory 540. At least part of these instructions are fetched from an instruction register 538 by a control logic 536 and interpreted according to the instruction set architecture of the CPU 430. Part of the instructions can also be directed to a register 532. In one implementation the instructions are decoded according to a hardwired method, and in another implementation the instructions are decoded according to a microprogram that translates instructions into sets of CPU configuration signals that are applied sequentially over multiple clock pulses. After fetching and decoding the instructions, the instructions are executed using an arithmetic logic unit (ALU) 534 that loads values from the register 532 and performs logical and mathematical operations on the loaded values according to the instructions. The results from these operations can be fed back into the register 532 and/or stored in a fast memory 540. According to certain implementations, the instruction set architecture of the CPU 430 can use a reduced instruction set architecture, a complex instruction set architecture, a vector processor architecture, or a very large instruction word architecture. Furthermore, the CPU 430 can be based on the Von Neuman model or the Harvard model. The CPU 430 can be a digital signal processor, a field programmable gate array (FPGA), an application specific integrated circuit (ASIC), a programmable logic array (PLA), a programmable logic device (PLD), or a complex programmable logic device (CPLD). Further, the CPU 430 can be an x86 processor by Intel or by AMD; an advanced RISC machines (ARM) processor; a POWER architecture processor by, e.g., IBM; a SPARC architecture processor by Sun Microsystems or by Oracle; or other known CPU architectures.

Referring again to FIG. 4, the data processing system 400 can include the SB/ICH 420 being coupled through a system bus to an I/O Bus, a read only memory (ROM) 456, universal serial bus (USB) port 464, a flash binary input/output system (BIOS) 468, and a graphics controller 458. PCI/PCIe devices can also be coupled to SB/ICH 420 through a PCI bus 462.

The PCI devices can include, for example, Ethernet adapters, add-in cards, and PC cards for notebook computers. The Hard disk drive 460 and CD-ROM 466 can use, for example, an integrated drive electronics (IDE) or serial advanced technology attachment (SATA) interface. In one implementation the I/O bus can include a super I/O (SIO) device.

Further, the hard disk drive (HDD) 460 and optical drive 466 can also be coupled to the SB/ICH 420 through a system bus. In one implementation, a keyboard 470, a mouse 472, a parallel port 478, and a serial port 476 can be connected to the system bus through the I/O bus. Other peripherals and devices can be connected to the SB/ICH 420 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

The functions and features described herein can also be executed by various distributed components of a system. For example, one or more processors can execute these system functions, wherein the processors are distributed across multiple components communicating in a network. The distributed components can include one or more client and server machines, which can share processing, such as a cloud computing system, in addition to various human interface and communication devices (e.g., display monitors, smart phones, tablets, personal digital assistants (PDAs)). The network can be a private network, such as a LAN or WAN, or can be a public network, such as the Internet. Input to the system can be received via direct user input and received remotely either in real-time or as a batch process. Additionally, some implementations can be performed on modules or hardware not identical to those described. Accordingly, other implementations are within the scope that can be claimed.

The functions and features described herein may also be executed by various distributed components of a system. For example, distributed performance of the processing functions can be realized using grid computing or cloud computing. Many modalities of remote and distributed computing can be referred to under the umbrella of cloud computing, including: software as a service, platform as a service, data as a service, and infrastructure as a service. Cloud computing generally refers to processing performed at centralized locations and accessible to multiple users who interact with the centralized processing locations through individual terminals.

Embodiments described herein provide guidance and instruction for a novice user during diagnostic measurement acquisition. A user may need many years of experience in order to determine reliable diagnostic results. In addition, several experienced users would be needed to determine reliable diagnostic results for multiple anatomical regions and diseases. For example, a first experienced user may recognize reliable results for a liver tumor diagnosis as a result of his/her vast experience in liver tumor diagnoses. A second experienced user may recognize reliable results in liver fibrosis as a result of his/her vast experience in liver fibrosis diagnoses. Other experienced users in various specialized areas of medicine would be needed to determine a reliable diagnostic result for each type of anatomical region and/or disease.

However, embodiments described herein determine reliable diagnostic results to a relatively inexperienced user across multiple anatomical regions and/or diseases. A user would simply need to know how to operate the diagnostic apparatus and how to interact with the real-time measurement acquisition guidance system. As a result, a relatively inexperienced user can determine reliable diagnostic results comparable to results determined by several experienced users across several different medical disciplines. A single inexperienced user can determine nearly identical reliable diagnostic results as several experienced users combined.

The foregoing discussion discloses and describes merely exemplary embodiments of the present disclosure. As will be understood by those skilled in the art, the present disclosure may be embodied in other specific forms without departing from the spirit or essential characteristics thereof. Accordingly, the present disclosure is intended to be illustrative, but not limiting of the scope of the disclosure, including the claims. The disclosure, including any readily discernible variants of the teachings herein, defines in part, the scope of the foregoing claim terminology, such that no inventive subject matter is dedicated to the public.

The invention claimed is:

1. An ultrasound apparatus, comprising:
    an ultrasound probe configured to transmit and receive ultrasonic waves; and
    processing circuitry configured to
    receive a single selected anatomical region-of-interest for a patient and an associated measurement protocol,
    perform measurement acquisition including acquisition of a plurality of measurement values on obtained ultrasound image data of the single selected anatomical region-of-interest for the patient, the plurality of measurement values being acquired at a plurality of positions within the single selected anatomical region-of-interest,
    generate at least one measurement result based upon a data-quality index that has been publicly disclosed, using the plurality of measurement values,
    display the generated at least one measurement result,
    calculate measurement metrics of the at least one measurement result by executing statistical processing using the plurality of measurement values, the measurement metrics indicating a statistical uncertainty of the at least one measurement result, and
    display the calculated measurement metrics along with guidance for an operator of the ultrasound apparatus, the guidance being determined based on the calculated measurement metrics and the at least one measurement result.

2. The ultrasound apparatus of claim 1, wherein the processing circuitry is further configured to
    determine whether the measurement metrics for the obtained ultrasound image data of the single selected anatomical region-of-interest are within a first predetermined range, and display, as the guidance, a message indicating a statistically uncertain result, when it is determined that the measurement metrics are not within the first predetermined range.

3. The ultrasound apparatus of claim 2, wherein the processing circuitry is further configured to
determine a plurality of statistical values, each of the plurality of statistical values corresponding to a respective measurement value of the plurality of measurement values and representing a statistical uncertainty of the respective measurement value within the single selected anatomical region-of-interest of a respective ultrasound image of the ultrasound image data,
determine whether measurement values of the plurality of statistical values for the obtained ultrasound image data are within a second predetermined range,
display out-of-range measurement values of the plurality of measurement values and out-of-range statistical values of the plurality of statistical values, and
display, as the guidance, a message indicating that measurement acquisition can be halted, when it is determined that the measurement metrics are within the first predetermined range.

4. The ultrasound apparatus of claim 2, wherein the processing circuitry is further configured to
determine a plurality of statistical values, each of the plurality of statistical values corresponding to a respective measurement value of the plurality of measurement values and representing a statistical uncertainty of the respective measurement value within the single selected anatomical region-of-interest of a respective ultrasound image of the ultrasound image data,
determine whether measurement values of the plurality of statistical values are within a second predetermined range, and
display, as the guidance, a message indicating which of the plurality of measurement values are statistically uncertain measurement values, when respective statistical values of the plurality of statistical values corresponding to the statistically uncertain measurement values are determined to not be within the second predetermined range.

5. The ultrasound apparatus of claim 4, wherein the processing circuitry is further configured to
determine whether a maximum number of measurement results has been obtained, and
display, as the guidance, a message indicating presence of a statistically uncertain result, when it is determined that the maximum number of measurement results has been obtained.

6. The ultrasound apparatus of claim 1, wherein the processing circuitry is further configured to
determine whether a minimum number of measurement results has been obtained, and
display, as the guidance, a message indicating to perform additional measurement acquisition, when it is determined that the minimum number of measurement results has not been obtained.

7. The ultrasound apparatus of claim 1, wherein the processing circuitry is further configured to determine whether to restart the measurement acquisition, select a different anatomical region-of-interest, or halt the measurement acquisition, when one or more of the data-quality index and/or the measurement metrics exceeds a threshold, thereby indicating that a failure state occurs.

8. The ultrasound apparatus of claim 1, wherein the processing circuitry is further configured to perform the measurement acquisition to generate the at least one measurement result by determining a measurement count for the single selected anatomical region-of-interest, the measurement count being a number of the measurement values to be acquired from the obtained ultrasound image data.

9. The ultrasound apparatus of claim 1, wherein the ultrasound probe includes
a transmitter configured to transmit the ultrasonic waves and
a receiver configured to receive reflected ultrasonic waves; and
the ultrasound apparatus further comprises an image generator configured to perform three-dimensional image processing to generate volume data based on the received reflected ultrasonic waves.

10. A method of determining reliable diagnostic results, the method comprising:
obtaining ultrasound image data from an ultrasound probe configured to transmit and receive ultrasonic waves;
receiving a single selected anatomical region-of-interest for a patient and an associated measurement protocol;
performing measurement acquisition including acquisition of a plurality of measurement values on the obtained ultrasound image data of the single selected anatomical region-of-interest for the patient, the plurality of measurement values being acquired at a plurality of positions within the single selected anatomical region-of-interest,
generating at least one measurement result based upon a data-quality index that has been publicly disclosed, using the plurality of measurement values;
displaying the generated at least one measurement result;
calculating, by processing circuitry, measurement metrics of the at least one measurement result by executing statistical processing using the plurality of measurement values, the measurement metrics indicating a statistical uncertainty of the at least one measurement result; and
displaying the calculated measurement metrics along with guidance for an operator of an ultrasound apparatus, the guidance being determined based on the calculated measurement metrics and the at least one measurement result,
wherein the guidance applied to the single selected anatomical region-of-interest is selected by one of the operator and the processing circuitry, based upon a statistical analysis of a parametric image representing, as a function of position, a predetermined parameter based on the ultrasound image data.

11. The method of claim 10, further comprising:
determining whether the measurement metrics for the obtained ultrasound image data of the single selected anatomical region-of-interest are within a first predetermined range; and
displaying, as the guidance, a message indicating a statistically uncertain result, when it is determined that the measurement metrics are not within the first predetermined range.

12. The method of claim 11, further comprising:
determining a plurality of statistical values, each of the plurality of statistical values corresponding to a respective measurement value of the plurality of measurement values and representing a statistical uncertainty of the respective measurement value within the single selected anatomical region-of-interest of a respective ultrasound image of the ultrasound image data;

determining whether measurement values of the plurality of statistical values for the obtained ultrasound image data are within a second predetermined range;

displaying out-of-range measurement values of the plurality of measurement values and out-of-range statistical values of the plurality of statistical values; and displaying, as the guidance, a message indicating that measurement acquisition can be halted, when it is determined that the measurement metrics are within the first predetermined range.

13. The method of claim 11, further comprising:

determining a plurality of statistical values, each of the plurality of statistical values corresponding to a respective measurement value of the plurality of measurement values and representing a statistical uncertainty of the respective measurement value within the single selected anatomical region-of-interest of a respective ultrasound image of the ultrasound image data;

determining whether measurement values of the plurality of statistical values are within a second predetermined range; and displaying, as the guidance, a message indicating which of the plurality of measurement values are statistically uncertain measurement values, when respective statistical values of the plurality of statistical values corresponding to the statistically uncertain measurement values are determined to not be within the second predetermined range.

14. The method of claim 13, further comprising:

determining whether a maximum number of measurement results has been obtained; and displaying, as the guidance, a message indicating presence of a statistically uncertain result, when it is determined that the maximum number of measurement results has been obtained.

15. The method of claim 10, further comprising:

determining whether a minimum number of measurement results has been obtained; and displaying, as the guidance, a message indicating to perform additional measurement acquisition, when it is determined that the minimum number of measurement results has not been obtained.

16. The method of claim 10, further comprising performing the measurement acquisition to generate the at least one measurement result by determining a measurement count based on the single selected anatomical region-of-interest obtained from reference data of previous images for the single selected anatomical region-of-interest, the measurement count being a number of the measurement values to be acquired from the obtained ultrasound image data.

17. A non-transitory computer-readable storage medium storing computer-readable instructions for execution by a computing device, the instructions comprising:

obtaining ultrasound image data;

receiving a single selected anatomical region-of-interest for a patient and an associated measurement protocol;

performing measurement acquisition including acquisition of a plurality of measurement values on the obtained ultrasound image data of the single selected anatomical region-of-interest for the patient, the plurality of measurement values being acquired at a plurality of positions within the single selected anatomical region-of-interest;

generating at least one measurement based upon a data-quality index that has been publicly disclosed, using the plurality of measurement values;

displaying the generated at least one measurement result;

calculating measurement metrics of the at least one measurement result by executing statistical processing using the plurality of measurement values, the measurement metrics indicating a statistical uncertainty of the at least one measurement result; and displaying the calculated measurement metrics along with guidance for an operator of an ultrasound apparatus, the guidance being determined based on the calculated measurement metrics and the at least one measurement result.

18. The non-transitory computer-readable storage medium of claim 17, storing computer-readable instructions, that when executed by the computing device, causes the processing circuitry to further perform:

determining whether the measurement metrics for the obtained ultrasound image data of the single selected anatomical region-of-interest are within a first predetermined range, and displaying, as the guidance, a message indicating a statistically uncertain result, when it is determined that the measurement metrics are not within the first predetermined range.

19. The non-transitory computer-readable storage medium of claim 18, storing computer-readable instructions, that when executed by the computing device, causes the processing circuitry to further perform:

determining whether a minimum number of measurement results has been obtained, and displaying, as the guidance, a message indicating to perform additional measurement acquisition, when it is determined that the minimum number of measurement results has not been obtained.

20. The ultrasound apparatus of claim 1, wherein the single selected anatomical region-of-interest is selected by one of the operator and the processing circuitry.

21. An ultrasound apparatus, comprising:

processing circuitry configured to:

obtain a plurality of ultrasound images, generate, for each of the plurality of ultrasound images, a respective measurement value for an anatomical region-of-interest within the each ultrasound image, to thereby generate a plurality of measurement values, generate, for each of the plurality of measurement values, a respective statistical value representing a statistical variation of the each measurement value within the anatomical region-of-interest of the each ultrasound image, to thereby generate a plurality of statistical values, accept respective measurement values of the plurality of measurement values in accordance with one or more acceptance criteria applied to the plurality of statistical values, to thereby determine accepted measurement values, and calculate a measurement result by combining the accepted measurement values to generate a combined measurement value as the measurement result.

* * * * *

UNITED STATES PATENT AND TRADEMARK OFFICE
CERTIFICATE OF CORRECTION

PATENT NO. : 10,905,402 B2
APPLICATION NO. : 15/221312
DATED : February 2, 2021
INVENTOR(S) : Gilles Daniel Joseph Guenette et al.

Page 1 of 1

It is certified that error appears in the above-identified patent and that said Letters Patent is hereby corrected as shown below:

On the Title Page

Item (71), the Applicant's name and address are incorrect. Item (71) should read:
-- (71) Applicant: CANON MEDICAL SYSTEMS CORPORATION, Otawara-shi (JP) --

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*